United States Patent [19]

Müller

[11] Patent Number: 5,374,697

[45] Date of Patent: Dec. 20, 1994

[54] SELECTED NOVEL SULFONIUM COMPOUNDS PARTICULARLY SUITABLE AS INITIATORS FOR THE THERMAL CURE OF CATIONICALLY POLYMERISABLE MATERIALS

[75] Inventor: Beat Müller, Marly, Switzerland

[73] Assignee: Ciba-Geigy Corporation, Ardsley, N.Y.

[21] Appl. No.: 91,803

[22] Filed: Jul. 14, 1993

[30] Foreign Application Priority Data

Jul. 21, 1992 [CH] Switzerland .................. 2291/92-2

[51] Int. Cl.$^5$ .................. C08G 59/02; C08K 5/36
[52] U.S. Cl. .................. 526/192; 526/222; 525/327.3; 525/502; 528/90; 528/139; 528/143; 528/236; 528/242; 528/356; 528/361; 528/365; 528/366; 528/393; 528/408; 528/409
[58] Field of Search .................. 528/90, 139, 143, 356, 528/361, 365, 366, 393, 408, 409, 236, 242; 525/502, 327.3; 526/192, 222

[56] References Cited

U.S. PATENT DOCUMENTS

| 4,058,401 | 11/1977 | Crivello | 96/115 |
| 4,216,288 | 8/1980 | Crivello | 528/90 |
| 4,251,521 | 2/1981 | Kathawala | 424/185 |
| 5,013,814 | 5/1991 | Roth et al. | 528/90 |
| 5,247,113 | 9/1993 | Roth et al. | 556/64 |

FOREIGN PATENT DOCUMENTS

0379464 7/1990 European Pat. Off. .
0508951 10/1992 European Pat. Off. .

OTHER PUBLICATIONS

Chemical Abstract 109: 232200n: "Epoxy Resin Curing Catalysts with Good Storage Stability".
Chemical Abstract 105: 208577n, "Convenient Preparation of Sulfonium Salts".
Chemical Abstract 94: 64822t, "Reactions of the Adducts of Thianthrene and Phenoxathiin Cation Radicals and Cyclohexene with Nucleophiles".
Journal of the American Chemical Society, vol. 95, No. 16, (1973) pp. 5311-5321.
Journal of the American Chemical Society, vol. 95, No. 16, (1973) pp. 5321-5334.
Journal of the American Chemical Society, vol. 100, No. 17, (1978) pp. 5512-5525.
Phosphorus, vol. 1, No. 2 (1971), pp. 93-95.
Chemische Berichte, vol. 118, No. 12, (1988) pp. 4830-4841.
The Chemistry of Heterocyclic Compounds, Part 2, (1966) p. 1864.
The Chemistry of Heterocyclic Compounds, Part 2, (1966) p. 1156.
Lange's Handbook of Chemistry, 13th Ed. (1985) Section 5, Tables, 5-6 & 5-7.
Houben-Weyl, vol. E11, p. 158 (1985).
Rodd's Chemistry of Carbon Compounds, 2nd Ed. vol. IV, Part A, (1973) p. 302.
Rodd's Chemistry of Carbon Compounds, 2nd Ed. vol. IV, Part E. (1977), p. 388.
The Journal of Organic Chemistry, vol. 53, No. 23, (1988) pp. 5571-5573.
The Journal of Organic Chemistry, vol. 49, No. 10, (1984), pp. 1824-1825.
Journal of the American Chemical Society, vol. 95, No. 16, (1973) pp. 5298-5307.

Primary Examiner—Frederick Krass
Attorney, Agent, or Firm—William A. Teoli, Jr.

[57] ABSTRACT

Sulfonium compounds of formula 1 or 2

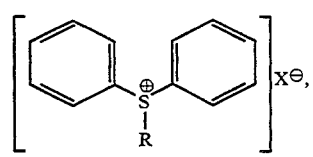

(Abstract continued on next page.)

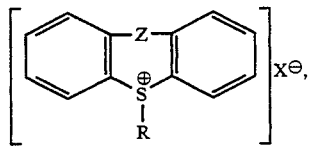

(2)

wherein
R is a mononuclear cycloalkyl radical containing 3 to 8 ring carbon atoms or a mononuclear cycloalkyl radical which contains 3 to 8 ring carbon atoms and to which at least one further ring containing carbon atoms is fused, X is a non-nucleophilic anion, and Z is a single bond, an oxygen or sulfur atom, a group of formula $>S^{\oplus}$—R $X^{\ominus}$, wherein R and X are as defined above, or is $>C=O$ or a methylene bridge, which sulfonium compounds are either unsubstituted or carry one or more than substituent selected from the group consisting of halogen, nitro, $C_1$–$C_8$alkyl, phenyl, hydroxyl, $C_1$–$C_8$alkoxy, phenoxy, benzyloxy, alkoxycarbonyl containing 1 to 4 carbon atoms in the alkoxy moiety or acyl of 1 to 12 carbon atoms.

7 Claims, No Drawings

SELECTED NOVEL SULFONIUM COMPOUNDS PARTICULARLY SUITABLE AS INITIATORS FOR THE THERMAL CURE OF CATIONICALLY POLYMERISABLE MATERIALS

The present invention relates to selected novel sulfonium compounds, to the use thereof, to thermally curable compositions containing said compounds, to a process for curing cationically polymerisable material, and to the cured material obtainable by said process.

Sulfonium salts of non-nucleophilic anions as initiators for curing cationically polymerisable materials have already been widely reported on in the literature.

Inter alia, U.S. Pat. No. 4,058,401 discloses salts of the general formula $[(R')_a(R'')_b(R''')_c)X]_d{}^+[MQ_e]^{-(e-f)}$, wherein R' is a monovalent aromatic radical R'', a monovalent organic radical selected from the group consisting of alkyl, cycloalkyl and substituted alkyl radicals, R''' is a polyvalent organic radical which, together with the atom X, forms a ring structure that is selected from aliphatic and aromatic radicals, X is a sulfur, selenium or tellurium atom, M is a metal atom or a metalloid atom, and Q is a halogen atom, and a is an integer from 0 to 3, b is an integer from 0 to 2, and c is 0 or 1, d is (e−f), e is greater than f and is an integer of up to 8, f corresponds to the valency of M which may be an integer from 2 to 7, and the sum of (a+b+c) is 3 or the valency of X. Salts of the above formula are proposed in particular for the radiation-induced curing of cationically polymerisable material. Although this US patent does postulate a thermal cure of cationically polymerisable material using such salts as initiators, temperatures in the range from 150° to 250° C. are said to be necessary. These temperatures, however, are far too high for the compounds to be considered suitable for use as thermal hardeners in actual practice.

Araliphatic sulfonium salts, on the other hand, have better suitability for the thermal cure of cationically polymerisable material. Sulfonium hardeners of this type, typically di- and tribenzylsulfonium salts, are disclosed, inter alia, in EP-A-0 379 464 U.S. Pat. No. 5,013,814). Thermally curable compositions based on araliphatic sulfonium compounds have good storage properties and are also fairly reactive (exothermic peak of the cure c. 110°–145° C.). Often, however, a still better reactivity/stability behaviour would be desirable, i.e. a greater reactivity (lower exothermic peak), while the compositions have the same or even better storage properties at room or moderately elevated temperature.

Surprisingly, it has now been found that a novel selected group of sulfonium compounds exhibits this enhanced reactivity/stability behaviour when they are used as thermal hardeners for cationically polymerisable material.

Accordingly, the invention relates to sulfonium compounds of formula (1) or (2)

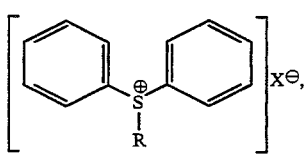

(1)

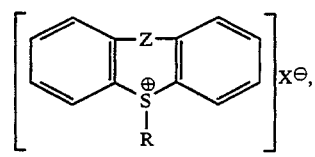

(2)

wherein
R is a mononuclear cycloalkyl radical containing 3 to 8 ring carbon atoms or a mononuclear cycloalkyl radical which contains 3 to 8 ring carbon atoms and to which at least one further ring containing carbon atoms is fused, X is a non-nucleophilic anion, and Z is a single bond, an oxygen or sulfur atom, a group of formula $>S^\oplus$—R X$^\ominus$, wherein R and X are as defined above, or is $>C=O$ or a methylene bridge, which sulfonium compounds are either unsubstituted or carry one or more than one substituent selected from the group consisting of halogen, nitro, $C_1$–$C_8$alkyl, phenyl, hydroxyl, $C_1$–$C_8$alkoxy, phenoxy, benzyloxy, alkoxycarbonyl containing 1 to 4 carbon atoms in the alkoxy moiety and acyl of 1 to 12 carbon atoms.

The novel sulfonium compounds have a relatively high activating energy for the thermal decomposition and therefore exhibit high latency in admixture with cationically polymerisable organic material and have enhanced storage properties at room and moderately elevated temperature, typically from 30° to 40° C. The compositions can nevertheless in practice be cured in the temperature range from 80° to 100° C. After exceeding a specific minimum temperature which is dependent on the individual compound, the polymerisation proceeds very rapidly, as, upon heating the mixtures, the range between the temperature at which the polymerisation reaction is initially clearly detectable and the temperature at which the polymerisation reaction has already reached its peak is very narrow and is normally in the range of only 15° to 30° C. A further advantage is the minor tendency of the novel sulfonium compounds to react with polymerisation inhibitors to form inactive products. Polymerisation inhibitors are usefully added to the compositions postulated in this invention whenever it is desired to prevent a premature cure during preparation, storage or processing that is caused by unwanted decomposition products of the sulfonium compounds. The use of polymerisation inhibitors for the intended purposes, which is subject matter of EP-A-0 508 951 (U.S. patent application Ser. No. 07/863,638 filed Apr. 6, 1992), now U.S. Pat. No. 5,296,567, will be discussed in more detail below.

Preferred compounds of formula (2) are those in which Z is a single bond, an oxygen or sulfur atom or a methylene bridge.

Very suitable cycloalkyl radicals R are typically cyclopropyl, cyclobutyl, cyclopentyl, cyclohexyl, cycloheptyl or cyclooctyl. Further rings may be fused to the cycloalkyl rings. Exemplary of such rings are bicyclo[2.2.1]hept-2-yl radicals or radicals of formula (3)

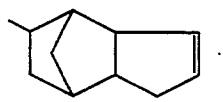

(3)

Non-nucleophilic anions are typically halide or perchlorate anions, but are preferably complex anions having the structure $[M(Hal)_n]^{(m-n)}$, where M is an atom of the third or fifth main group of the Periodic Table of the Elements, preferably B, P, As, Sb, and Hal is halogen, preferably chloro or fluoro, and m is the number of the main group to which M belongs. In some cases, one or more than one halogen atom can be replaced by a hydroxide group. Also suitable are the anions of aromatic or aliphatic sulfonic acids, preferably of halogenated, more particularly of perfluorinated aliphatic sulfonic acids. The most preferred anions X are $BF_4^-$, $PF_6^-$, $AsF_6^-$, $SbF_6^-$, $SbF_5(OH)^-$ and $CF_3SO_3^-$.

As mentioned, the novel sulfonium compounds may be unsubstituted or may carry one of the above mentioned substituents. The substituents may be located at any suitable position of the molecule, and in particular the radical R may also carry one or more than one of the cited substituents.

Especially preferred are sulfonium compounds of formula I if R is a radical of formula (3), (4) or, preferably, (5)

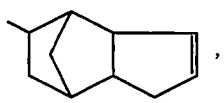  (3)

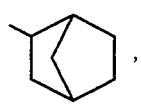  (4)

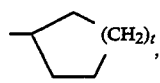  (5)

wherein t is either 1, 2 or 3. In these compounds the radical R preferably carries no substituent.

Finally, most preferred are compounds of formula (6)

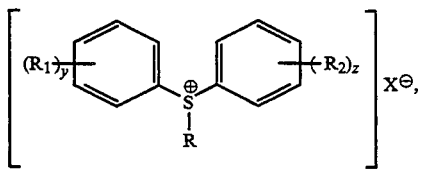  (6)

wherein X is $PF_6^-$, $AsF_6^-$, $SbF_6^-$, $SbF_5(OH)^-$, and is preferably $SbF_6^-$, R is a radical of formula (3), (4) or (5) as defined above and is unsubstituted, $R_1$ and $R_2$ are each independently of the other hydroxyl, phenoxy or $C_1$-$C_8$alkoxy, preferably methoxy or ethoxy, and y and z are each independently of the other either 0 or 1. If these sulfonium compounds carry substituents $R_1$ and/or $R_2$, said substituents are most preferably in para-position to the sulfonium group.

The novel compounds can be prepared by known processes. For example, diphenyl sulfide or a compound of formula

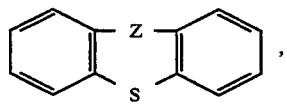

wherein Z has the given meaning, or a derivative of these compounds substituted e desired manner, can be reacted in the presence of a strong acid, e.g. $H_2SO_4$, $HPF_6$, $BF_4$(etherate), $HClO_4$ or $CF_3SO_3H$, with at least an equimolar amount of a suitable cycloalkene (i.e. of the cycloalkene whose formula corresponds to the desired radical R in the final sulfonium compound and which contains an olefinic double bond that starts from the carbon atom attached in the final compound to the sulfonium sulfur) and then, if desired, reacted with an alkali metal salt or a quaternary ammonium salt of the desired anion X.

Other suitable processes for the preparation of the compounds are disclosed, inter alia, in initially cited EP-A-0 379 464 (U.S. Pat. No. 5,013,814).

Diphenyl sulfide and the compounds of formula

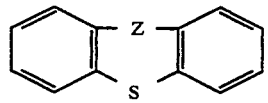

and derivatives thereof are known compounds some of which are commercially available.

Diphenyl sulfides are described, inter alia, Houben-Weyl, Vol. 9, page 93 (1955) or Vol. E11, p. 158 (1985).

Compounds of formel

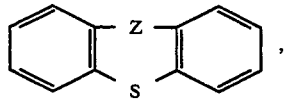

in which Z is a single bond (dibenzothiophenes) and processes for their preparation are described, inter alia, in Rodd's Chemistry of Carbon Compounds, 2nd Ed. (Editor S. Coffey), Vol. IV, Part A, Elsevier Scientific Publishing Company, Amsterdam London New York, (1973), p. 302 et seq.; compounds of the indicated formula in which Z is a methylene bridge (dibenzothiopyranes) or a >C=O— group are described in Rodd's Chemistry of Carbon Compounds, 2nd Ed. (Editor S. Coffey), Vol. IV, Part E, Elsevier Scientific Publishing Company, Amsterdam London New York, (1977), p. 388 et seq.; the compounds of this formula in which Z is an oxygen atom (phenoxathiines), are described in Heterocyclic Compounds, Multisulfur and Sulfur and Oxygen Five and Six Membered Heterocycles, Part Two, Interscience Publishers (a division of John Wiley & Sons), New York (1966), p. 864 et seq.; and, finally, the corresponding compounds in which Z is a sulfur atom (thiantrenes) are also described in Heterocyclic Compounds, Multisulfur and Sulfur and Oxigen Five and Six Membered Heterocycles, Part Two, Interscience Publishers (a division of John Wiley & Sons), New York (1966), p. 1156 et seq.

As the compounds of formulae (1) and (2) are particularly useful hardeners and hardening initiators for the thermal cure of cationically polymerisable materials, the invention also relates to the use of said compounds as initiators for the thermal cure of cationically polymerisable material and a thermally curable composition comprising (a) at least one cationically polymerisable material and (b) at least one of the aforementioned sulfonium compounds.

The novel compositions preferably contain at least one sulfonium compound of formula (1) above, most preferably of formula (6).

Cationically polymerisable materials suitable for the novel compositions are typically those of the following types, which materials may be used singly or as mixtures of at least two components:
1. Ethylenically unsaturated compounds which are polymerisable by a cationic mechanism, including:
   1. Mono- and diolefins, e.g. isobutylene, butadiene, isoprene, styrene, α-methylstyrene, divinyl benzenes, N-vinylpyrrolidone, N-vinylcarbazole and acrolein.
   2. Vinyl ethers, e.g. methyl vinyl ether, isobutyl vinyl ether, trimethylolpropane trivinyl ether, ethylene glycol divinyl ether; cyclic vinyl ethers, e.g. 3,4-dihydro-2-formyl-2H-pyran (dimeric acrolein) and the 3,4-dihydro-2H-pyran-2-carboxylic acid ester of 2-hydroxymethyl-3,4-dihydro-2H-pyran.
   3. Vinyl esters, e.g. vinyl acetate and vinyl stearate.
II. Cationically polymerisable heterocyclic compounds, e.g. ethylene oxide, propylene oxide, epichlorhydrin, glycidyl ethers of monohydric alcohols or phenols, e.g. n-butyl glycidyl ether, n-octyl glycidyl ether, phenyl glycidyl ether and cresyl glycidyl ether; glycidyl acrylate, glycidyl methacrylate, styrene oxide and cyclohexene oxide; oxetanes such as 3,3-dimethyloxetane and 3,3-di(chloromethyl)oxetane; tetrahydrofuran; dioxolanes, trioxane and 1,3,6-trioxacyclooctane; lactones such as β-propiolactone, γ-valerolactone and ε-caprolactone; thiiranes such as ethylene sulfide and propylene sulfide; epoxy resins; linear and branched polymers containing glycidyl groups in the side chains, e.g. homo- and copolymers of polyacrylate and polymethacrylate glycidyl esters.

Among these aforementioned polymerisable compounds, the epoxy resins and, in particular, the di- and polyepoxides and epoxy resin prepolymers of the type used for the preparation of crosslinked epoxy resins are especially important. The di- and polyepoxides can be aliphatic, cycloaliphatic or aromatic compounds. Illustrative examples of such compounds are the glycidyl ethers and β-methyl glycidyl ethers of aliphatic or cycloaliphatic diols or polyols, typically those of ethylene glycol, 1,2-propanediol, 1,3-propanediol, 1,4-butanediol, diethylene glycol, polyethylene glycol, polypropylene glycol, glycerol, trimethylolpropane or 1,4-dimethylolcyclohexane or of 2,2-bis(4-hydroxycyclohexyl)propane, the glycidyl ethers of di- and polyphenols, typically resorcinol, 4,4'-dihydroxydiphenylmethane, 4,4'-dihydroxydiphenyl-2,2-propane, novolaks and 1,1,2,2-tetrakis(4-hydroxyphenyl)ethane.

Other industrially important glycidyl compounds are the glycidyl esters of carboxylic acids, preferably of di- and polycarboxylic acid. Illustrative examples thereof are the glycidyl esters of succinic acid, adipic acid, azelaic acid, sebacic acid, phthalic acid, terephthalic acid, tetra- and hexahydrophthalic acid, isophthalic acid or trimellitic acid, or of dimerised fatty acids.

Exemplary of polyepoxides that differ from glycidyl compounds are the diepoxides of vinyl cyclohexene and dicyclopentadiene, 3-(3',4'-epoxycyclohexyl)-8,9-epoxy-2,4-dioxaspiro[5.5]undecane, the 3',4'-epoxycyclohexylmethyl ester of 3,4-epoxycyclohexanecarboxylic acid, butadiene diepoxide or isoprene diepoxide, epoxidised linoleic acid derivatives or epoxidised polybutadiene.

Preferred epoxy resins are diglycidyl ethers or advanced diglycidyl ethers of dihydric phenols or of dihydric aliphatic alcohols of 2 to 4 carbon atoms. Particularly preferred epoxy resins are the diglycidyl ethers or advanced diglycidyl ethers of 2,2-bis(4-hydroxyphenyl)propane and bis(4-hydroxyphenyl)methane.

Hence those compositions referred to above in which the cationically polymerisable material is an epoxy resin constitute a special embodiment of the invention.

Suitable cationically polymerisable compounds are also phenolic plastics.

Preferred phenolic plastics are resols prepared from a phenol and an aldehyde. Suitable phenols include phenol itself, resorcinol, 2,2-bis(p-hydroxyphenyl)propane, p-chlorophenol, a phenol substituted by one or two alkyl groups each containing 1 to 9 carbon atoms, including o-, m- and p-cresol, the xylenols, p-tert-butylphenol and p-nonylphenol, as well as phenyl-substituted phenols, preferably p-phenylphenol. The aldehyde condensed with the phenol is preferably formaldehyde; but other aldehydes such as acetaldehyde and furfural are also suitable. If desired, a mixture of such curable phenol/aldehyde resins can be used.

The preferred resols are condensates of phenol, p-chlorophenol, resorcinol or o-, m- or p-cresol with formaldehyde.

The amount of sulfonium compounds in the compositions is normally 0.05 to 20 percent by weight, based on the cationically polymerisable material, preferably 1 to 15, most preferably 1 to 5, percent by weight.

The compositions may also a solvent or dispersing agent for the curing initiator. Preferred solvents are the diesters of aromatic dicarboxylic acids, in particular dibutyl phthalate.

The novel compositions may contain, especially if the cationically polymerisable compound is an epoxy resin, further thermal hardeners such as polycarboxylic acids, polycarboxylic anhydrides, such as hexahydrophthalic acid anhydride or methylhexahydrophtalic acid anhydride, or polyphenols. The amount of such an additional hardener is smaller than the stoichiometric amount which would be required for the full cure of the cationically polymerisable material of the composition if the additional hardener would be used alone.

Furthermore, the curable mixtures of this invention may comprise still further compounds that copolymerise with the cationically polymerisable material used, typically cyclic ethers or cyclic lactones, as reaction solvents. Illustrative examples of such reaction solvents are propylene carbonate, ε-caprolactone, γ-butyrolactone or tetrahydrofurfuryl alcohol. When using copolymerisable compounds, the amount thereof is normally from 1 to 50% by weight, based on the amount of cationically polymerisable material, and the amount of curing initiator is normally from 0.05 to 20% by weight, based on the amount of cationically polymerisable material and copolymerisable compound.

The compositions may also contain known additives conventionally used in the technology of polymerisable materials. Illustrative examples of such additives are coinitiators, typically secondary or tertiary diols, pigments, dyes, fillers such as talcum, kaolin, mica, gypsum, titanium dioxide, quartz powder, cellulose, diatomaceous earth, ground dolomite, wollastonite, silica of large specific surface area (Areosil ®), powdered polyvinyl chloride, polyolefins as well as metal powders such as copper, silver, aluminium or iron powder, reinforcing agents, glass fibres and other fibres, flame retardants such as antimony trioxide and aluminium trihydrate, which is preferably used in an amount of 50 to 70 percent by weight, based on the entire composition, and antistatic agents, flow control agents, antioxidants and light stabilisers.

Particularly useful additives are the aforementioned polymerisation inhibitors. The use of a polymerisation inhibitor in the novel compositions enables (especially moisture-induced) decomposition products of the initiator to be reacted such that they can no longer interfere with the processing and cure of the compositions. In addition, the thermal stability of the compositions can be enhanced for a limited time.

A particularly preferred embodiment of the novel thermally curable compositions therefore contains as additional component (c) a polymerisation inhibitor in such a minor amount that the composition contains an excess of sulfonium compounds (over the amount of inhibitor) sufficient for the cure.

Suitable polymerisation inhibitors are normally compounds that are stronger nucleophiles than the cationically polymerisable material and react more rapidly with the protons in the composition or with the cations of the growing polymer chain than the monomers of the polymerisable material, so that protons and cations cannot initiate any further polymerisation of said material.

Particularly suitable polymerisation inhibitors are bases that are able to neutralise the strong Bronstedt acids which are formed by the initiator compounds during the thermal cure and also during storage by decomposition caused by moisture or impurities, for example in the solvent or dispersant of the initiator component, on the lines of an acid/base reaction. As the cited Bronstedt acids are usually very strong acids such as $HSbF_6$ or $HPF_6$, it is also possible to use as base many compounds which intrinsically exhibit acid reaction in water, typically tetrabutylammonium hydrogen sulfate. Preferred bases are those having a pKa value of about 2 to 12 (at 25° C. in water). Illustrative examples of such bases may be readily inferred from the standard tabular reference works of chemistry, inter alia Lange's Handbook of Chemistry (Editor John A. Dean), 13th Ed. (1985), McGraw-Hill Book Company, New York, Section 5, Tables 5–6 and 5–7. The eligible bases can be solid, conveniently basic fillers, typically unwashed aluminium trihydrate. The bases may, however, also be liquid, as typically many amines.

Amines are an especially preferred group of polymerisation inhibitors. These amines shall preferably have a pKa value of 2 to 9 (25° C. in water). Suitable amines are primary, secondary and also tertiary amines. The term "amine" shall be understood in this context as also meaning heterocycles, in which the amino nitrogen is a member of the heterocycle, conveniently pyrazoles, imidazoles, pyrrolidines, pyrrolines, imidazolidines, imidazolines, pyrazolidines, pyrazolines, piperidines, piperazines, indolines, morpholines, quinuclidine, 1,8-diazabicyclo[5.4.0]undec-7-ene, 1,5-diazabicyclo[4.3.0]non-5-ene or 1,4-diazabicyclo[2.2.2]octane.

Particularly preferred amines are secondary and, more especially, tertiary amines, which include tribenzylamine, 1-methylimidazole, 1,8-diazabicyclo[5.4.0]undec-7-ene, 1,5-diazabicyclo[4.3.0]non-5-ene and 1,4-diazabicyclo[2.2.2]octane.

Particularly suitable amines for use in the practice of this invention are those selected from the group consisting of ($c_1$) aromatic amines containing from one to four $NH_2$ groups and having at least one substituent in ortho-position to each each amino group, which substituent is selected from $C_1$–$C_{10}$alkyl, $C_1$–$C_{10}$alkoxy, $C_5$–$C_6$cycloalkyl, $C_6$–$C_{10}$aryl or halogen, with the proviso that the amine is not substituted in both ortho-positions to an amino group by halogen, and ($c_2$) aromatic amines containing up to four 4 $NH_2$ groups and having one substituent in ortho-or para-position to each each amino group, which substituent is selected from among —COOH, —COOR, —COR, —$SO_2$R or —SOR, and R is $C_1$–$C_{10}$alkyl, $C_5$–$C_6$cycloalkyl, $C_6$–$C_{10}$aryl, aminoaryl or —R'—OOC—$C_6H_4$—$NH_2$, where R' is alkylene.

Such compounds containing 2, 3 or 4 $NH_2$ groups may be prepared by condensation of a suitably substituted aniline with aldehydes or ketones, conveniently with formaldehyde [subgroup ($c_1$)] or by reaction of an amino acid with compounds which carry 2–4 OH groups capable of ester condensation [subgroup ($c_2$)].

The aromatic amines of subgroups ($c_1$) and ($c_2$) may be mononuclear or binuclear. The binuclear compounds may contain fused as well as non-fused rings.

The alkyl substituents and alkyl moieties of the alkoxy substituents of the amines of subgroup ($c_1$) may be straight-chain or branched. Illustrative examples of suitable alkyl groups are methyl, ethyl, n- and isopropyl, butyl, pentyl, hexyl, octyl or decyl. Illustrative examples of alkoxy groups are the alkoxy groups corresponding to the alkyl groups. Illustrative examples of suitable cycloalkyl groups are cyclopentyl or cyclohexyl. Illustrative examples of aryl groups are phenyl or naphthyl. Illustrative examples of suitable halogen substituents are iodo, bromo and, preferably, chloro.

Preferred amines of subgroup ($c_1$) carry one or two $NH_2$ groups and have a pKa value of 3–4.5 and carry at least one alkyl substituent in ortho-position to each amino group. Especially preferred amines of subgroup ($c_1$) are 2,6-dialkylanilines or compounds of formula (II)

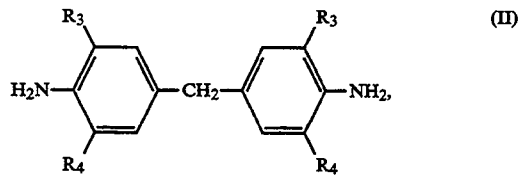

wherein $R_3$ is chloro or $C_1$–$C_3$alkyl, and $R_4$ is hydrogen or $C_1$–$C_3$alkyl, preferably 2,6-diisopropylaniline, or compounds of formula (II), wherein $R_3$ and $R_4$ are each independently of the other $C_1$–$C_3$alkyl, preferably ethyl or isopropyl.

Illustrative examples of especially suitable amines of group are ($c_1$) sind 2,6-diisopropylaniline, 3-amino-2,4-diethyl-6-methylaniline, bis(4-amino-3,5-diethylphenyl)methane, bis(4-amino-3-methyl-5-isopropylphenyl)methane, bis(4-amino-3,5-diisopropylphenyl)methane, bis(4-amino-3-ethyl-5-methylphenyl)methane, bis(4-amino-3,5-diethylphenyl)methane, bis(4-amino-3-methylphenyl)methane and bis(4-amino-3-chlorophenyl)methane.

The substituents in ortho- or para-position relative to the amino group of subgroup (c₂) are electrophilic groups.

If the substituent R in the definition of the amines (c₂) is $C_1$-$C_{10}$alkyl, $C_5$-$C_6$cycloalkyl or $C_6$-$C_{10}$aryl, what has been said above in connection with the corresponding substituents of the amines of subgroup (c₁) will apply to this substituent.

R defined as amoinoaryl is preferably aminoaryl containing 6 to 10 ring carbon atoms, conveniently aminonaphthyl or aminophenyl, typically 1-amino-4-naphthyl, 2-amino-6-naphthyl, 2-amino-7-naphthyl, or 2-, 3- and, preferably, 4-aminophenyl.

If R is a group —R'—OOC—$C_6H_4NH_2$, R' is preferably $C_2$-$C_{10}$alkylene and the amino group is preferably in para-position at the phenyl ring.

Preferred amines of the subgroup (c₂) are compounds containing one or two $NH_2$ groups and having a pKa value of 2–3.5. Illustrative examples of preferred compounds are anthranilic acid or compounds of formula (III)

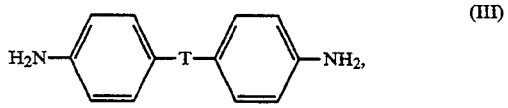

wherien T is CO, SO and, preferably, $SO_2$ or —COO(CH₂)$_m$OOC—, where m=2–6, preferably m=2.

Suitable examples of such compounds are 4-aminobenzoic acid, anthranilic acid, bis(4-aminophenyl)sulfone, bis(4-aminophenyl)sulfoxide, bis(4-aminophenyl)ketone or 1,3-propanediol-bis(4-aminobenzoate).

The curable compositions may contain amines per se or prereacted with an epoxy resin. This prereaction is preferably carried out at elevated temperature, typically in the range from 100° to 200° C. This variant of the invention may be expedient if an epoxy resin is used as cationically polymerisable material. Preferred embodiments of the invention are, however, those comprisng the use of amines which have not been prereacted with an epoxy resin.

The polymerisation inhibitor c) may only be used in the practice of this invention in an amount so minor that the composition contains an excess of initiator sufficient for curing the composition. The excess of initiator should preferably be at least 0.05 to 5% by weight, based on the cationically polymerisable material, but may also be higher. If customary amounts of initiator are used, the inhibitor will be used in an amount substantially below the amount equivalent to the free cations or acid protons which the initiator is able to form. The polymerisation inhibitor can therefore be used typically in an amount of 0.01 to 0.5 equivalent, based on the total amount of initiator in the novel compositions, and will conveniently be used in an amount of 0.01 to 0.15 equivalent.

The polymerisation inhibitor can be added at any time before bringing together the initiator and the polymerisable material, even immediately before. It reacts almost at once with the decomposition products of the initiator thereby introduced into the composition or formed afterwards, so that the decomposition products do not act as non-latent hardener for the polymerisable material.

Many polymerisation inhibitors additionally effect an increase in temperature necessary for the start of the cure. This is tantamount to an increase in the thermal stability of the composition. Illustrative examples of such inhibitors are tribenzylamine, bis(4-amino-3-ethyl-5-methylphenyl)methane, 1,8-diazabicyclo[5.4.0]undec-7-ene or 1,5-diazabicyclo[4.3.0]non-5-ene, which exhibit the effect especially when using sulfonium initiators. By means of DSC measurements it is possible to detect such substances easily from the displacement of the start of the cure peak to higher temperatures which these compositions exhibit in comparison with compositions of the same type without inhibitor. The novel compositions can be processed at higher temperature than corresponding inhibitor-free compositions and handled at a given temperature for substantially longer than the latter. By adding to a specific composition inhibitors of the given type in increasing amount it is usually possible to attain an ever greater rise in the temperature required for the start of the cure. It is thus possible to control the thermal stability of the compositions over a wide range. As, however, the inhibitor is present in the novel compositions in an amount equivalent to a fraction of the total amount of initiator and ceases to react almost completely before a reaction of the polymerisable material occurs, the actual cure of the composition, which is ultimately effected by excess initiator, is no longer influenced by the addition of the initiator. This is shown in the DSC diagram by the exothermic peak of the cure reaction being not, or substantially not, displaced.

Illustrative examples of polymerisation inhibitors that exhibit or only minimally exhibit the above described effect are 1-methylimidazole, 1.4-diazabicyclo[2.2.2]octane and 3-amino-2,4-diethyl-6-methylaniline.

The temporary increase in thermal stability by using polymerisation inhibitors in the practice of this invention can naturally also be useful if the novel compositions are freshly prepared and their storage is not planned or is also more unproblematical, as in the case of solid compositions. The invention can therefore be used with advantage for the fabrication of fibrous composite structures. For this utility, the novel compositions make it possible for a limited time to heat the matrix resins safely to a higher temperature during application, thereby resulting in lower viscosities and hence in better penetration of the fibre material with the matrix, or they permit the use of less or no diluent or solvent at all in the composition. Likewise, casting resins heated to a higher temperature and thus less viscous greatly simplify filling casting moulds which have complicated and fine structures. In the same way, the thermal homogenisation of solid one-component systems, for example of powder coating compositions or thermosetting solid adhesive formulations, with thermally stable formulations, can be better and more safely effected, as already described in the introduction.

When applying the practice of the present invention to two-component compositions, i.e. when the component containing the initiator and the component containing the cationically polymerisable material are separately prepared and stored, it is expedient to add the polymerisation inhibitor to the component containing the polymerisable material. The amount of polymerisation inhibitor in this partial component can vary, but is ordinarily from 0.01 to 5% by weight, based on the resin. For the cure, the initiator must be added in to this partial component in an amount such that the final composition contains an excess of initiator over the amount of inhibitor which is sufficient to cure the composition.

These compositions are therefore typically prepared by A) homogenising the sulfonium compounds with a solvent or dispersant suitable therefor, B) homogenising a polymerisation inhibitor as component c) with the cationically polymerisable organic material, temporarily storing the partial mixtures obtained in partial steps A) and/or B), and D) mixing both partial mixtures with each other.

In addition, optional molecular sieve materials can be added to a solvent-based initiator component, in particular zeolites, as they are able to slow down the deactivation of the initiator by decomposition by absorbing, inter alia, the residual water in this component. The storage properties of the hardener can thereby be additionally enhanced. The zeolite material preferably has a particle size of c. 3 to 5 μm and a pore size of 0.3 to 0.7 nm, and can be used in an amount of 0.1 to 20% by weight, preferably 0.1 to 10% by weight, based on the curing initiator.

The novel compositions can basically be obtained in any form, typically as homogeneous liquid mixtures or in homogeneous or inhomogeneous vitreous form. Homogeneous vitreous products can be obtained in per se known manner by liquefying solid cationically polymerisable organic materials, with or without the addition of suitable solvents, heating to temperatures above their glass transition point, adding initiator and optional inhibitor, as well as cooling the resulting mixtures.

The novel compositions can be rapidly cured at low temperature. The exothermic peak of the cure reaction of the compositions is normally below 120° C., and often in the range from 50° to 100° C. The exothermic peak can be determined in conventional manner with a differential scanning calorimeter. The novel compositions can also be subjected to a precure at low temperature until the curable composition gels, after which a full cure is carried out at elevated temperature.

The cure is ordinarily carried out while simultaneously shaping the compositions to mouldings, impregnations, coatings or bonds.

The novel compositions can be used quite generally for making cured products and can be used in a formulation adapted to each particular end use typically as surface-coating compositions, paints and lacquers, also powder coating compositions, moulding compounds, dipping resins, casting resins, impregnating resins, laminating resins, one- or two-pack adhesives or matrix resins, especially for encapsulating or impregnating objects.

The use of the novel compositions, also in the form of a low pressure moulding compound, for impregnating and/or encapsulating objects, especially electrical high-tension or low-tension components or electronic components, is especially preferred, as is also their utility as liquid or solid coating compositions, typically paints or lacquers or powder coating compositions, their utility for making low pressure moulding compounds, their utility as part of composite systems for circuit boards or as matrix for fibrous composite structures and, finally, their utility as thermosetting adhesives.

The products obtained from the novel compositions by thermal curing have good allround properties, have a high glass transition temperature and temperature resistance, and are solid, insoluble and infusible three-dimensionally crosslinked products.

EXAMPLE 1

Preparation of cyclohexyldiphenylsulfonium hexafluoroantimonate 1 mol of diphenyl sulfide is dissolved in an excess of cyclohexene and and to the solution is added 1 mol of $HBF_4$ (54% etherate) and the mixture is stirred at room temperature. After c. 15 minutes a second phase forms. The product is isolated by addition of ether and dissolved in acetone. Afterwards, sodium hexafluoroantimonate is added to the solution and the resulting cyclohexyldiphenylsulfonium hexafluoroantimonate is precipitated by addition of water. The compound has a melting point of 129° C. and the analytical data obtained are as follows:

|   | found | calculated |
|---|---|---|
| C: | 42.8% | 42.8% |
| H: | 4.24% | 4.19% |
| S: | 6.55% | 6.35% |
| NMR (dissolved in $CDCl_3$) | | |
| 4H | 8.0 ppm (d) | |
| 6H | 7.7 ppm (d) | |
| 1H | 4.6 ppm (m) | |
| 10H | 1.1–1.8 ppm (m) | |

EXAMPLE 2

To 9 parts by weight of an epoxy resin consisting of a mixture of bisphenol A and bisphenol F with a viscosity of 6500–8000 mPa.s (at 25° C., DIN 53015) and an epoxide equivalent of 172–182 g/eq (ARALDIT ® PY 302-2) is added one part by weight of a solution containing 10% by weight of a sulfonium compound of the following formula in dibutyl phthalate

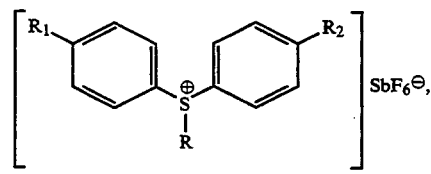

wherein R, $R_1$ and $R_2$ have the meanings indicated in Table 1. The temperatures indicated in the Table of the start of the (exothermic) cure reaction, of the exothermic peak, of the total energy and of the residual energy above 130° C. can be gathered from the DSC diagram.

TABLE 1

| Sulfonium compound | | | Start of | Exothermic | Total | Residual |
|---|---|---|---|---|---|---|
| R | $R_1$ | $R_2$ | cure | peak | energy | energy |
| cyclopentyl | H | H | 65° C. | 95° C. | 537 J/g | 24 J/g |
| cyclohexyl | H | H | 75° C. | 98.,8° C. | 512.3 J/g | 21.4 J/g |

TABLE 1-continued

| Sulfonium compound | | | Start of cure | Exothermic peak | Total energy | Residual energy |
|---|---|---|---|---|---|---|
| R | $R_1$ | $R_2$ | | | | |
| (norbornyl) | OCH₃ | OCH₃ | 65° C. | 95.2° C. | 507.2 J/g | 54.8 J/g |
| (dicyclic) | H | H | 50° C. | 81.7° C. | 502.3 J/g | 24.1 J/g |

EXAMPLE 3

A resin component of the following composition is prepared:

37.36% parts by weight of ARALDIT ® PY 302-2 (epoxy resin consisting of a mixture of bisphenol A and bisphenol F with a viscosity of 6500–8000 mPa.s (at 25° C., DIN 53015) and an epoxide equivalent of 172–182 g/eq 0.01% by weight of 1-methylimidazole (polymerisation inhibitor)

0.31% by weight of SILAN ® 187 A (glycidoxypropyl trimethoxysilane)

0.05% by weight of a conventional silicone-free de-aerator 0.10% by weight of BENTONE ® SD2 (organically modified montmorrillonite)

62.17% by weight of APYRAL ® 2E (aluminium trihydrate)

Sulfonium compounds of the same general formula as indicated in Example 2 in which R, $R_1$ and $R_2$ are as defined in Table 2 are dissolved in dibutyl phthalate (concentration 15.66%). 3.78 parts by weight of each of these solutions are mixed with 100 parts of the above resin component. The values indicated in Table 2 can be gathered from the DSC diagram.

TABLE 2

| Sulfonium compound | | | Start of cure | Exothermic peak | Total energy | Residual energy |
|---|---|---|---|---|---|---|
| R | $R_1$ | $R_2$ | | | | |
| cyclopentyl | H | H | 87.4° C. | 105.3° C. | 198.4 J/g | 13.4 J/g |
| cyclohexyl | H | H | 95° C. | 115.5° C. | 193.0 J/g | 8.5 J/g |

What is claimed is:

1. A thermally curable composition comprising (a) at least one cationically polymerisable material and (b) a thermal hardener consisting essentially of at least one sulfonium compound of formula (1)

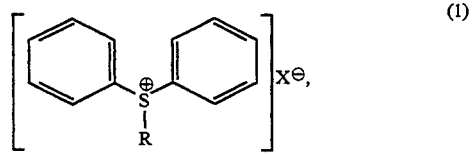

R is a mononuclear cycloalkyl radical containing 3 to 8 ring carbon atoms or a mononuclear cycloalkyl radical which contains 3 to 8 ring carbon atoms and to which at least one further ring containing carbon atoms is fused, X is a non-nucleophilic anion, and which sulfonium compound is either unsubstituted or carries one or more than one substituent selected from the group consisting of $C_1$–$C_8$alkyl, phenyl, $C_1$–$C_8$alkoxy, phenoxy, and benzyloxy.

2. A composition according to claim 1, which contains a sulfonium compound of formula (1) wherein R is a radical of formula (3), (4), or (5)

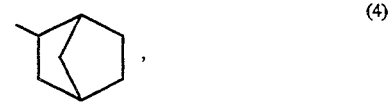

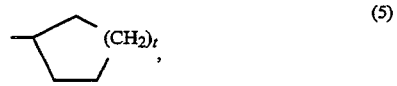

wherein t is either 1, 2 or 3.

3. A composition according to claim 2, which contains a sulfonium compound of formula (6)

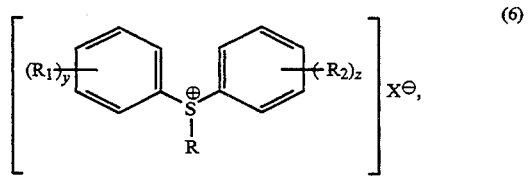

wherein X is $PF_6^-$, $AsF_6^-$, $SbF_6^-$, or $SbF_5(OH)^-$, R is a radical of formula (3), (4) or (5), $R_1$ and $R_2$ are each independently of the other phenoxy of $C_1$–$C_8$alkoxy, and y and z are each independently of the other either 0 or 1.

4. A composition according to claim 1 in which the cationically polymerisable material is an epoxy resin.

5. A composition according to claim 1 which comprises as additional component (c) a stabilizing effective amount of a polymerisation inhibitor which is present in such a small amount that sufficient sulfonium compound (b) unaffected by it remains to effect curing of the composition.

6. Cured material obtained by heating the composition of claim 1 until cure is complete.

7. A composition according to claim 3 which contains a sulfonium compound of formula (6), wherein X is $SbF_6^-$ and $R_1$ and $R_2$ are each independently of the other methoxy or ethoxy.

* * * * *